US008615366B2

(12) United States Patent  
Galley et al.

(10) Patent No.: US 8,615,366 B2
(45) Date of Patent: Dec. 24, 2013

(54) HANDHELD DIABETES MANAGEMENT DEVICE WITH BOLUS CALCULATOR

(75) Inventors: Paul J. Galley, Cumberland, IN (US); Richard W. Wilson, Fortville, IN (US); John F. Price, McCordsville, IN (US); Alan M. Greenburg, Indianapolis, IN (US); Marshall Parker, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 226 days.

(21) Appl. No.: 12/976,507

(22) Filed: Dec. 22, 2010

(65) Prior Publication Data
US 2012/0095318 A1    Apr. 19, 2012

Related U.S. Application Data

(60) Provisional application No. 61/393,519, filed on Oct. 15, 2010.

(51) Int. Cl.
*G01N 33/48* (2006.01)
*G01N 31/00* (2006.01)
*G06G 7/48* (2006.01)
*G06G 7/58* (2006.01)

(52) U.S. Cl.
USPC .................... 702/19; 702/22; 703/11; 703/12

(58) Field of Classification Search
None
See application file for complete search history.

(56) References Cited

U.S. PATENT DOCUMENTS

| 7,291,107 | B2 | 11/2007 | Hellwig et al. |
| 7,553,281 | B2 | 6/2009 | Hellwig et al. |
| 7,869,851 | B2 * | 1/2011 | Hellwig et al. ............... 600/345 |
| 2004/0172284 | A1 | 9/2004 | Sullivan et al. |
| 2006/0047192 | A1 | 3/2006 | Hellwig et al. |
| 2006/0137695 | A1 | 6/2006 | Hellwig et al. |
| 2008/0058628 | A1 | 3/2008 | Hellwig et al. |
| 2008/0139910 | A1 | 6/2008 | Mastrototaro et al. |
| 2009/0030733 | A1 | 1/2009 | Cohen et al. |
| 2009/0036753 | A1 | 2/2009 | King |
| 2009/0105570 | A1 | 4/2009 | Sloan et al. |
| 2010/0057043 | A1 | 3/2010 | Kovatchev et al. |
| 2010/0160757 | A1 | 6/2010 | Weinert et al. |
| 2010/0160759 | A1 | 6/2010 | Celentano et al. |
| 2010/0161346 | A1 * | 6/2010 | Getschmann et al. ............ 705/2 |
| 2010/0168660 | A1 | 7/2010 | Galley et al. |

(Continued)

FOREIGN PATENT DOCUMENTS

WO    2009/048462    4/2009

*Primary Examiner* — Larry D Riggs, II
(74) *Attorney, Agent, or Firm* — Harness, Dickey

(57) ABSTRACT

A method for monitoring blood glucose (bG) levels of a diabetic user. The method may be implemented on a non-transitory computer readable medium adapted to run on a processing subsystem, the processing subsystem forming a portion of a handheld diabetes management device for monitoring the bG levels of a diabetic user and determining a correction bolus to be provided to the user. The method may comprise using a memory to store information in a plurality of different time blocks. The information may include a plurality of differing user defined health events that each include a predetermined associated percentage value set by the user by which a correction bolus calculation will be modified to account for one of an increase or a decrease in insulin associated with each one of the defined health events. The processing subsystem may be used to communicate with the memory and to obtain the information and to calculate therefrom the correction bolus.

25 Claims, 11 Drawing Sheets

(56) References Cited

U.S. PATENT DOCUMENTS

| | | |
|---|---|---|
| 2010/0204557 A1 | 8/2010 | Kiaie et al. |
| 2010/0212675 A1 | 8/2010 | Walling et al. |
| 2010/0218132 A1 | 8/2010 | Soni et al. |
| 2010/0249530 A1 | 9/2010 | Rankers et al. |
| 2010/0331650 A1 | 12/2010 | Batman |

\* cited by examiner

FIG. 3B

Health

150 →

| Health List Item |
| Health List Item |
| Health List Item |
| Health List Item |
| Health List Item |
| Health List Item |

Bar

| Cancel | Save |

FIG. 3C

Enter Health

152 — ☐ Fasting
       -10%

☐ 🏃 Exercise 1
     +10%

☐ 🏃 Exercise 2
     +20%

☐ 💊 Illness
     +10%

152 — ☐ ☹ Stress
         +30%

☐ ♀ Premenstrual
     -10%

← 150a

| Cancel | Confirm |

HANDHELD DIABETES MANAGEMENT DEVICE WITH BOLUS CALCULATOR

CROSS-REFERENCE TO RELATED APPLICATIONS

This application claims the benefit of U.S. Provisional Application No. 61/393,519, filed on Oct. 15, 2010. The entire disclosure of the above application is incorporated herein by reference.

FIELD

This disclosure relates to diabetes care medical devices used for diagnostics and therapy, and more particularly to a handheld diabetes management device incorporating a bolus calculator including a plurality of customizing features that the user may use to generate a recommended bolus or a suggested carbohydrate amount that takes into account recurring and/or non-recurring health and lifestyle events associated with the user.

BACKGROUND

The statements in this section merely provide background information related to the present disclosure and may not constitute prior art.

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and may be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. Its incidence is increasing rapidly, and it is estimated that between 2005 and 2030, the number of deaths from diabetes will double. In the United States, nearly 24 million Americans have diabetes with an estimated 25 percent of seniors age 60 and older being affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Management of diabetes is complex as the level of blood glucose entering the bloodstream is dynamic. The variation of insulin that controls the transport of glucose out of the bloodstream also complicates diabetes management. Blood glucose levels are sensitive to diet and exercise, but also can be affected by sleep, stress, smoking, travel, illness, menses, and other psychological and lifestyle factors unique to individual patients. The dynamic nature of blood glucose and insulin, and all other factors affecting blood glucose, often require a person with diabetes to understand ongoing patterns and forecast blood glucose levels (or at least understand the actions that raise or lower glucose in the body). Therefore, therapy in the form of insulin or oral medications, or both, can be timed to maintain blood glucose levels in an appropriate range.

Management of diabetes is often highly intrusive because of the need to consistently obtain reliable diagnostic information, follow prescribed therapy, and manage lifestyle on a daily basis. Daily diagnostic information, such as blood glucose, is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an insulin pen, an ambulatory infusion pump, or a combination of such devices. With insulin therapy, determining the amount of insulin to be injected can require forecasting meal composition of carbohydrates, fat and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data that are acquired from medical devices, personal healthcare devices, patient recorded information, healthcare professional tests results, prescribed medications and recorded information. Medical devices including self-monitoring bG meters, continuous glucose monitors, ambulatory insulin infusion pumps, diabetes analysis software, and diabetes device configuration software each of which generates or manages or both large amounts of diagnostic and prescriptive data. Personal healthcare devices include weight scales, pedometers and blood pressure cuffs. Patient recorded information includes information relating to meals, exercise and lifestyle as well as prescription and non-prescription medications. Healthcare professional biomarker data includes HbA1C, fasting glucose, cholesterol, triglycerides and glucose tolerance. Healthcare professional recorded information includes therapy and other information relating to the patient's treatment.

There is a need for a handheld patient device to aggregate, manipulate, manage, present, and communicate diagnostic data and prescriptive data from medical devices, personal healthcare devices, patient recorded information, biomarker information and recorded information in an efficient manner to improve the care and health of a person with diabetes, so the person with diabetes can lead a full life and reduce the risk of complications from diabetes.

Additionally, there is a need for a handheld diabetes management device that is able to provide an even more accurate bolus recommendation to the user based on various user inputs that take into account current activities and a current health of the user, and which is also highly customizable by the user to thus enhance the accuracy, convenience and efficiency of the device in generating a recommended bolus or a suggested carbohydrate amount for the user.

SUMMARY

Further areas of applicability will become apparent from the description provided herein. It should be understood that the description and specific examples are intended for purposes of illustration only and are not intended to limit the scope of the present disclosure.

In one implementation the present disclosure relates to a method for monitoring blood glucose (bG) levels of a diabetic user. The method may be implemented on a non-transitory computer readable medium adapted to run on a processing subsystem, the processing subsystem forming a portion of a handheld diabetes management device for monitoring the bG levels of a diabetic user and determining a correction bolus to be provided to the user. The method may comprise using a memory to store information in a plurality of different time blocks. The information may include: an upper target bG value for each one of the plurality of different time blocks, defined by the user, during a twenty four hour period; a lower target bG value for each one of the plurality of different time blocks during the twenty four hour period; a hypoglycemic warning value, defined by the user, representing a hypoglycemic bG value for the user; a conversion factor for converting from glucose to insulin; a plurality of differing user defined health events that each include a predetermined associated percentage value set by the user by which a correction bolus calculation will each be modified to account for one of an increase or a decrease in insulin associated with each one of the differing health events; and a carbohydrate value input by the user in connection with a meal. The processing subsystem may be used to communicate with the memory and to obtain the information and to calculate therefrom the correction bolus.

In another implementation the present disclosure relates to a method implemented on a non-transitory computer readable medium adapted to run on a processing subsystem, the processing subsystem forming a portion of a handheld diabetes management device for monitoring blood glucose (bG) levels of a diabetic user and determining a total bolus to be provided to the user. The method may comprise using a memory to store: an upper target bG value for each one of a plurality of different time blocks during a twenty four hour period; a lower target bG value for each one of the plurality of different time blocks during the twenty four hour period; a maximum allowed bG value representing a currently corrected for bG value of the user, which is computed from prior bG history records; a plurality of user defined health events including an exercise event, a stress event and an illness event, with each one of the health events including a predetermined associated percentage value selected by the user by which a preliminary bolus calculation will be modified to account for one of an increase or a decrease in insulin associated with the health event; and a carbohydrate value input by the user in connection with a meal. The processing subsystem may be used to communicate with the memory and obtain the upper target bG value, the lower target bG value, the maximum allowed bG value, one of the user defined health events, and the carbohydrate value input by the user; and to calculate therefrom: a meal bolus calculated based on the carbohydrate value input by the user, the meal bolus representing an amount of insulin needed to compensate for the carbohydrate value representing the meal; a correction bolus representing an additional amount of insulin needed beyond the insulin represented by the meal bolus; and a total bolus value obtained by summing the meal bolus and the correction bolus to obtain a summed bolus value. And then, for each of the meal bolus and the correction bolus, the summed bolus value may be modified in accordance with the percentage value of a user selected one of the user defined health events. The correction bolus, the meal bolus, the total bolus value and the maximum allowed bG value may be displayed to the user on a display of the device.

In still another aspect the present disclosure relates to a customizable, handheld diabetes management device for monitoring blood glucose (bG) levels of a diabetic user and determining a total bolus to be provided to the user. The device may comprise a housing adapted to be held in a hand of the user, and a memory contained in the housing and configured to store information including: an upper target bG value for each one of a plurality of different time blocks defined by the user during a twenty four hour period; a lower target bG value for each one of the plurality of different time blocks during the twenty four hour period; a plurality of differing user defined health events that each include a predetermined associated percentage value set by the user by which a meal bolus calculation and a correction bolus calculation will each be modified to account for one of an increase or a decrease in insulin associated with each one of the differing health events; and a carbohydrate value input by the user in connection with a meal. A processing subsystem contained in the housing is in communication with the memory. The processing subsystem is adapted to obtain the information from the memory and to calculate therefrom the meal bolus, the correction bolus and a recommended total bolus that is a sum of the calculated meal bolus and the calculated correction bolus. A display system contained in the housing may be used for displaying a plurality of fields that the user is able to configure to include the information, and also for displaying the recommended total bolus to the user.

BRIEF DESCRIPTION OF THE DRAWINGS

The following figures are selected embodiments of the handheld diabetes manager with enhanced data capability and related system embodiments and information.

FIG. 3B is a drawing illustrating an example screen for enabling a user to program in various health events to be considered by the device when providing bolus recommendations;

FIG. 3C is an illustration showing how the display of the device may display the various programmed health event options after same are programmed into the device;

DETAILED DESCRIPTION

The following description is merely exemplary in nature and is not intended to limit the present disclosure, application, or uses.

Figure 1:
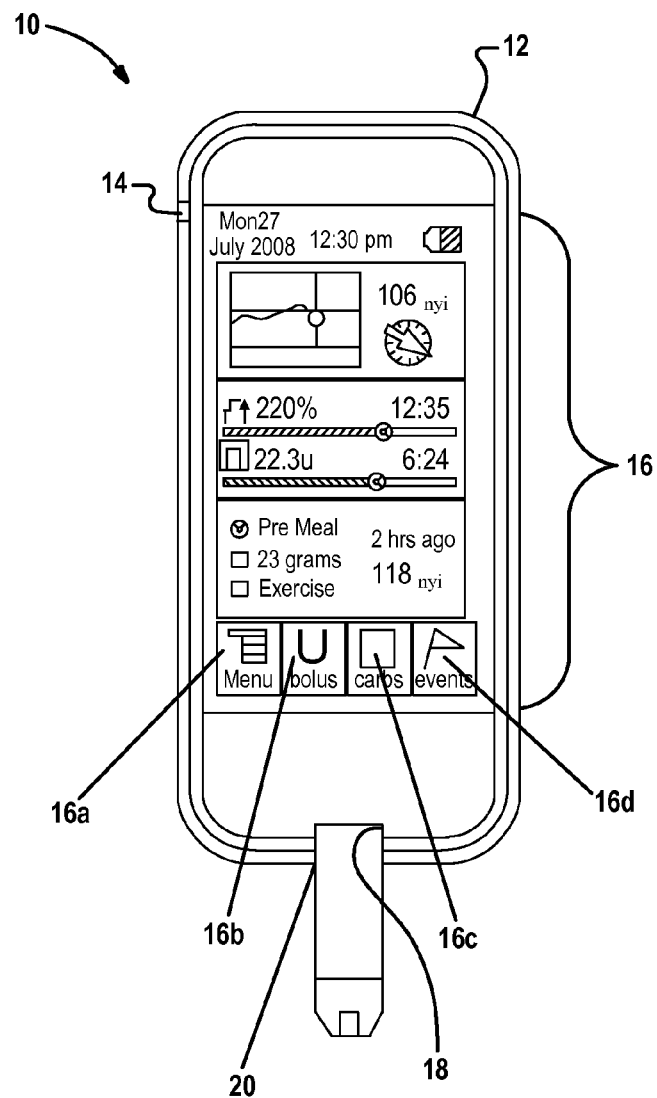
FIG. 1 is a perspective view of one embodiment of a handheld diabetes bG management device in accordance with the present disclosure.

Referring to FIG. 1, there is shown a high level drawing of one embodiment of a handheld, portable blood glucose (bG) monitoring device 10 that may be used in implementing a bolus calculation or carbohydrate suggestion. Typically the device 10 includes a housing 12 that may contain user unit control switches 14 (e.g., ON/OFF), a touchscreen display 16, and a port 18 into which a bG test strip 20 may be inserted. The display 16 may display user selectable options for allowing the user to access a software driven menu 16a of various selections, a selection 16b for allowing the user to enter bolus information, a selection 16c for enabling the user to enter carbohydrate information for snacks or meals, and a selection 16d for allowing the user to enter information pertaining to events (e.g., meals, exercise, periods of stress, periodic physiological events such as a menstrual cycle, etc.) that may affect the user's bG measurement being read by the device 10. Although the display 16 will be described herein as a touchscreen display, it will be appreciated that any other suitable form of display may be incorporated (e.g., LED, etc.). If a touchscreen display is not used, the user control switches 14 may need to include specific buttons or controls by which the user is able to select various options and input markers needed to carry out the bolus calculation or carbohydrate suggestion. It will be appreciated that the above is a high level description of the device 10, and in practice the device may include additional controls, input ports, output ports, etc., as may be desired to even further enhance the utility of the device 10 or its use with other components and devices (e.g., laptop computers, infusion pumps, etc.). Accordingly, the above description of the device 10 should not be taken as limiting its construction or features in any way.

Figure 2:
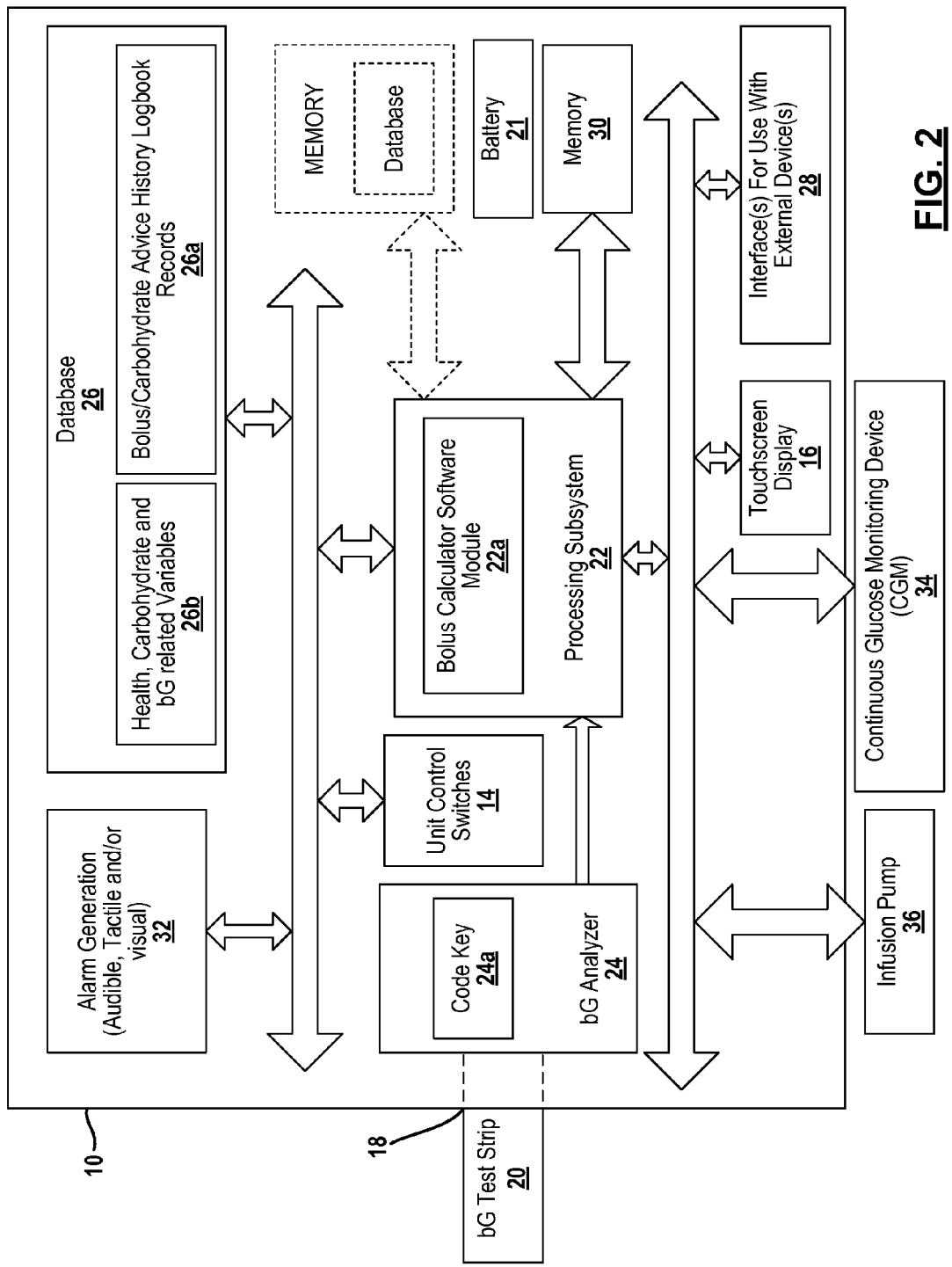
FIG. 2 is a high level block diagram of various components and subsystems that may be incorporated in the device shown in FIG. 1.

Referring to FIG. 2, a high level block diagram of the device 10 is shown. The device 10 can include a rechargeable or non-rechargeable battery 21 for powering the various electronic components of the device 10. A processing subsystem 22 (e.g., a microprocessor based subsystem) is included that receives information from a bG analyzer 24. The bG analyzer 24 is located adjacent the port 18 of the housing 12 to permit the bG analyzer 24 to read the bG test strip 20. The bG analyzer 24 can include a code key 24a that includes calibration information for the bG test strip 20 being read. The processing subsystem 22 can also be in communication with a database 26 that is used to store bG test values obtained from the bG analyzer 24 and other important health related information for the user. In particular, the database 26 can include a subsection 26a for storing recommended bolus and carbohydrate advice history records that are still active in their influence of current and future advice, and a section 26b for storing health, carbohydrate and bG related variables (e.g., insulin sensitivities of the user for various time segments of the day) pertinent to the user. It will be appreciated that the database 22 will be formed by a non-volatile memory.

The processing subsystem 22 can also be in communication with the display 16, the user control switches 14, and one or more interfaces 28 for interfacing the device 10 to other external devices. The processing subsystem 22 can also be in communication with a memory (such as a RAM) 30 for storing various types of information (e.g., meal and bed times) that are input by the user, as well as any other information requiring temporary or permanent storage. However, it will be appreciated that the database 26 and the memory 30 could be implemented in a single memory device (e.g., RAM) if desired, as indicated in phantom in FIG. 2. The processing subsystem 22 can be in communication with an alarm generation subsystem 32 that is used to generate an alarm consisting of audible signals, tactile signals (e.g., a vibration signal) or possibly even visual signals such as illuminated lights (e.g., LEDs) on the device 10. The processing subsystem 22 can also receive inputs from a remote continuous glucose monitoring ("CGM") device 34 secured to the user's body such that device 10 is continually updated with glucose information for the user. Finally the processing subsystem 22 can be in communication with a remote insulin infusion pump 36 (either through a wired or wireless RF connection) being worn by the user so that the device 10 is able to communicate bolus information to the infusion pump 36. By "remote" it is meant that the CGM device 34 and the infusion pump 36 are each located outside of the device 10 but otherwise still in communication with the device 10.

The device 10 can be used to implement a non-transitory machine readable code, for example a software module 22a, that is run by the processing subsystem 22. The software module 22a can be formed as a single module or as a collection of independent modules that run concurrently on the processing subsystem 22. The processing subsystem 22, working in connection with the software module 22a, receives a wide variety of user: inputs applied by the user through the touchscreen display 16 to generate a recommended meal bolus, a recommended correction bolus, a recommended total bolus, or when appropriate a suggested carbohydrate amount. The suggested carbohydrate amount may be provided in response to the detection by the device 10 of a hypoglycemic bG test value. The operations and capabilities of the device 10 will be explained in detail in the following paragraphs. The device 10 significantly enhances the convenience and ease of use to the user through the implementation of a plurality of customizable inputs that enable the user to program the device 10 with unique health information pertinent to the user. More specifically, the device 10 allows the user to program the device 10 with health information which even more completely enables the device 10 to take into account unique health conditions affecting the user, as well as regular occurring and non-regular occurring health events that could otherwise have an impact on the bolus and carbohydrate calculations made by the device 10.

Figure 3A:
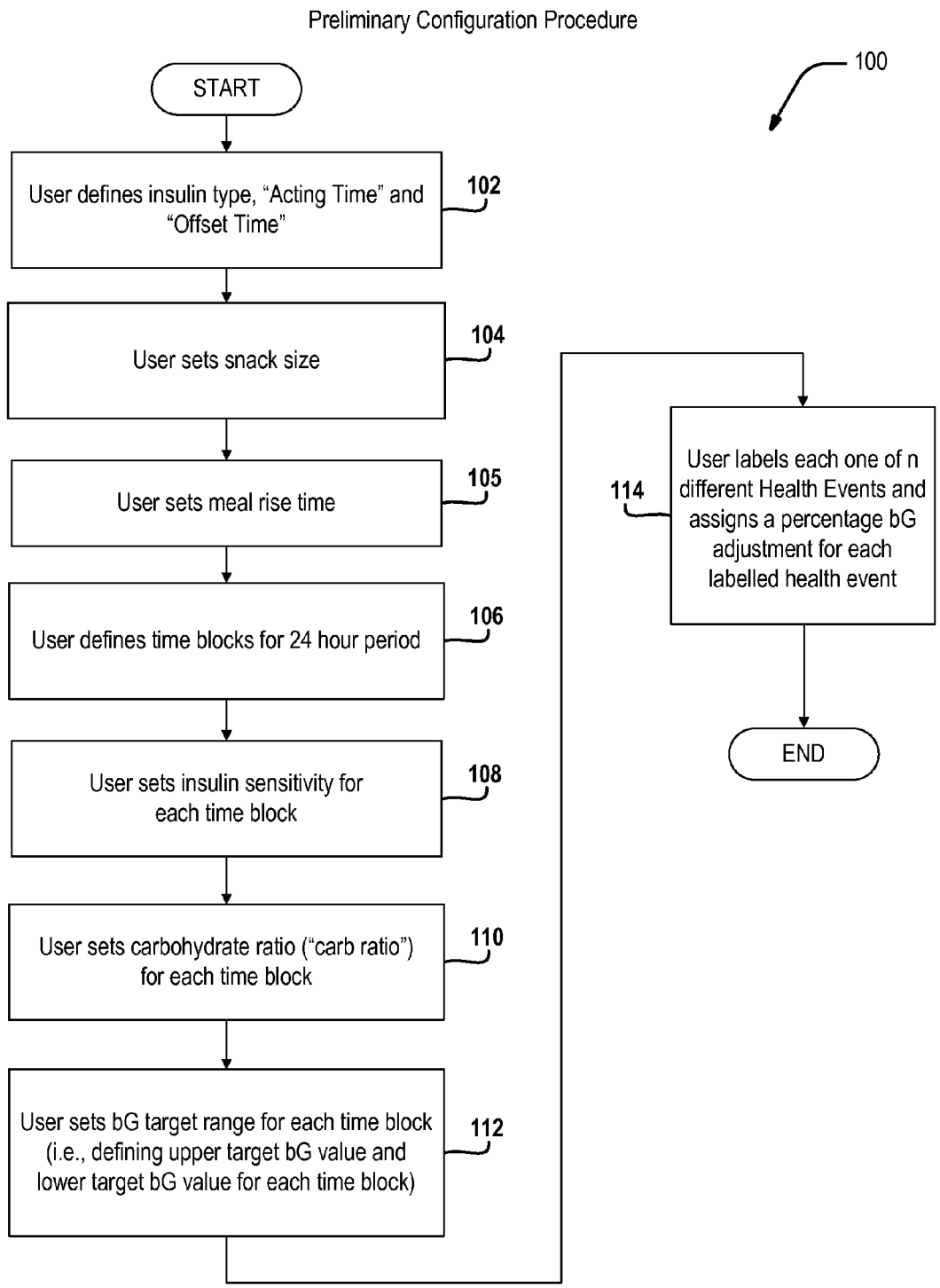
FIG. 3A is an exemplary flowchart illustrating a preliminary configuration procedure for configuring the device shown in FIG. 1.

Referring to FIG. 3A, a flowchart 100 illustrates an exemplary preliminary configuration procedure that the user can perform to configure the various inputs needed to tailor the device 10 to the requirements of the user. At operation 102 the user can define the insulin type that she/he is using, as well as the "acting time" and "offset time" associated with the specified insulin. The user also sets a snack size at operation 104. Any carbohydrate amount greater than the snack size that the user enters into the device 10 will be considered as a "meal" by the device 10 if the amount exceeds the user defined snack size. A meal rise glucose amplitude (expressed in bG units) is also defined by the user at operation 105. At operation 106 the user can define the various time blocks for a twenty four hour period. In one exemplary implementation the user may define up to eight contiguous or non-contiguous time blocks during a twenty four hour period. However, it will be appreciated that a greater or lesser number of time blocks could be provided for. Since the user's insulin sensitivity will be assumed to vary over the course of the day, the user can set a different insulin sensitivity value for each time block, as indicated at operation 108. At operation 110 the user can set a carbohydrate ratio ("carb ratio") for each time block as well, as this ratio can be assumed to vary for different users throughout the course of a day. At operation 112 the user can set a bG target range for each time block, as this range is also presumed to vary slightly over the course of a day. The bG target range is made up of an upper target bG value and a lower target bG value which define the upper and lower bounds, respectively, of the bG target range. It will also be appreciated that the processing subsystem 22 operates to consider an action shape of a previously taken correction bolus, where the action shape is defined by a bG lowering potential of the previously taken correction bolus, as well as the offset time and the acting time of the insulin associated with the previously taken correction bolus. The action shape is considered by the processing subsystem 22 when generating a new bolus recommendation.

At operation 114 the user labels each one of up to n different health events with a label using the touchscreen display 16 and assigns a percentage bG adjustment for each labeled health event. It is a valuable feature of the device 10 that the user is able to program these various percentage adjustments for each of a plurality of user defined health events that the user knows in advance will affect her/his bG test values. For example, the user may program the device with different bG percentage adjustment values for health events such as "exercise", "illness"; "stress", or even for recurring conditions such as a menstrual cycle. The precise percentages selected by the user for each user defined health event can be based on past history and experience of the user or based in part on the advice of a health care professional who is helping the user to manage her/his blood glucose levels. As one example, if the user knows from experience that an exercise event performed right after a meal will reduce a needed meal bolus by about 20%, then the user may enter "−20" in a displayed field on the display 16. The processing subsystem 22 will thereafter use this 20% reduction in calculating the meal bolus and the correction bolus when the exercise event has been selected. These features will be defined in greater detail in the following paragraphs.

Figure 3D:
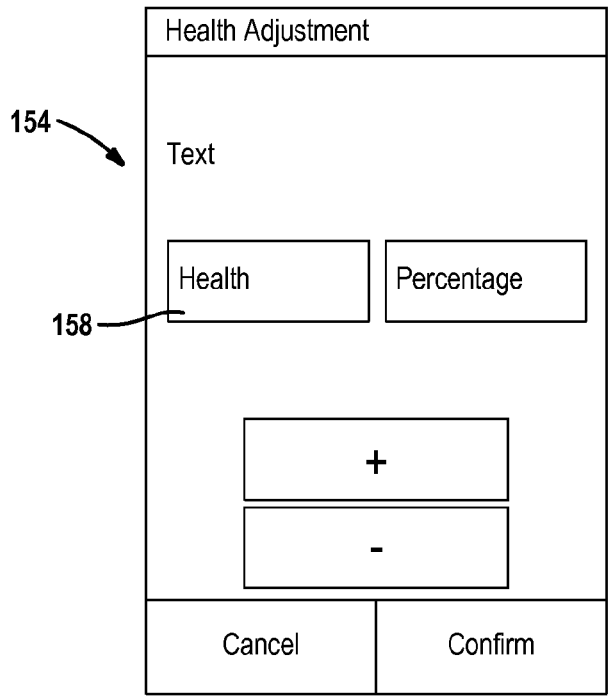
FIG. 3D is a drawing of an exemplary layout that may be presented on the display of the device for allowing the user to enter text that describes the health event being programmed, along with the percentage adjustment to be made to the health event.
Figure 3E:
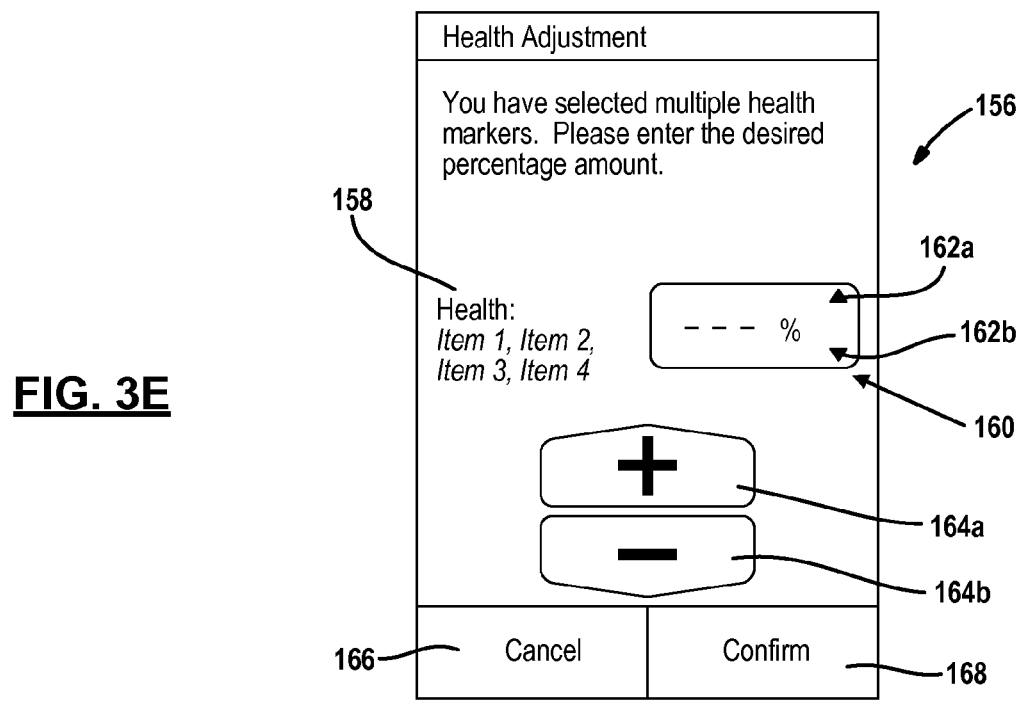
FIG. 3E is an illustration showing how the display of the device may display a message to the user if the user has selected more than one health event, and allows the user to enter a custom health adjustment percentage to be applied to a bolus calculation.
Figure 3F:
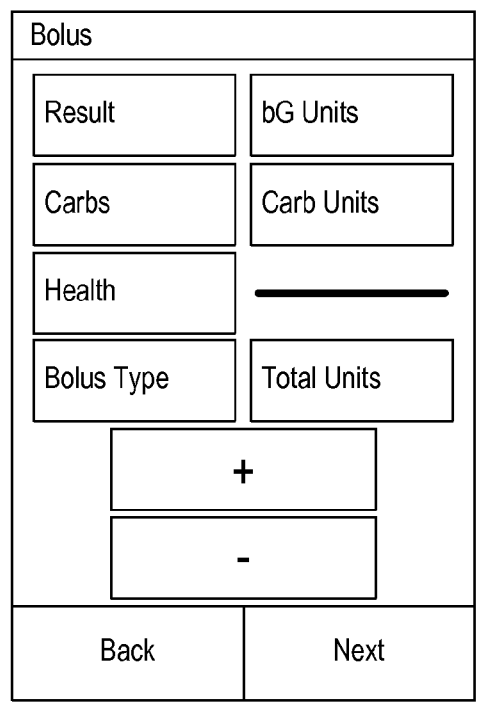
FIG. 3F is a drawing showing an exemplary layout of how various items of information may be presented to the user on the display of the device.

Referring to FIGS. 3B-3F, illustrations are presented of how the various forms of information can be displayed to the user on the display 16 of the device 10. FIG. 3B shows a screen 150 that presents multiple "Health List Item" boxes that may be displayed in the display 16 when the user has chosen to assign a specific health event to a bG test value that she/he has just obtained. FIG. 3C shows a screen display 150a illustrating how this information can appear on the display 16. The user can select one of the boxes 152 in FIG. 3C, which will mark the just-obtained bG test value with the user programmed specific health event, and thus apply the user programmed percentage adjustment to the just-obtained bG test value. If the user selects two or more health events for a single bG test value, then the device 10 can display a different screen that forces the user to select a "custom" health event percentage that will be applied to the just-obtained bG test value. Such a screen layout 154 is shown in FIG. 3D. An actual exemplary screen display 156 is shown in FIG. 3E that corresponds to the screen layout 154. The "Health" field 158 in FIG. 3E displays all the health events that the user has checked off in boxes 152 of screen display 150a of FIG. 3C. In field 160 the user can enter and/or adjust a custom health percentage adjustment using the arrows 162a and 162b. Arrows 164a and 164b may also be displayed, which are used to enable the user to increase or decrease a suggested bolus. User control 166 enables the user to cancel the health event adjustment and control 168 enables the user to confirm the selection (i.e., apply) of the custom health percentage in field 160. FIG. 3F illustrates how various items of information (e.g., bG test value; carbohydrate information; health adjustment percentage; and recommended bolus) can be displayed to the user on the display 16.

Figure 4A:
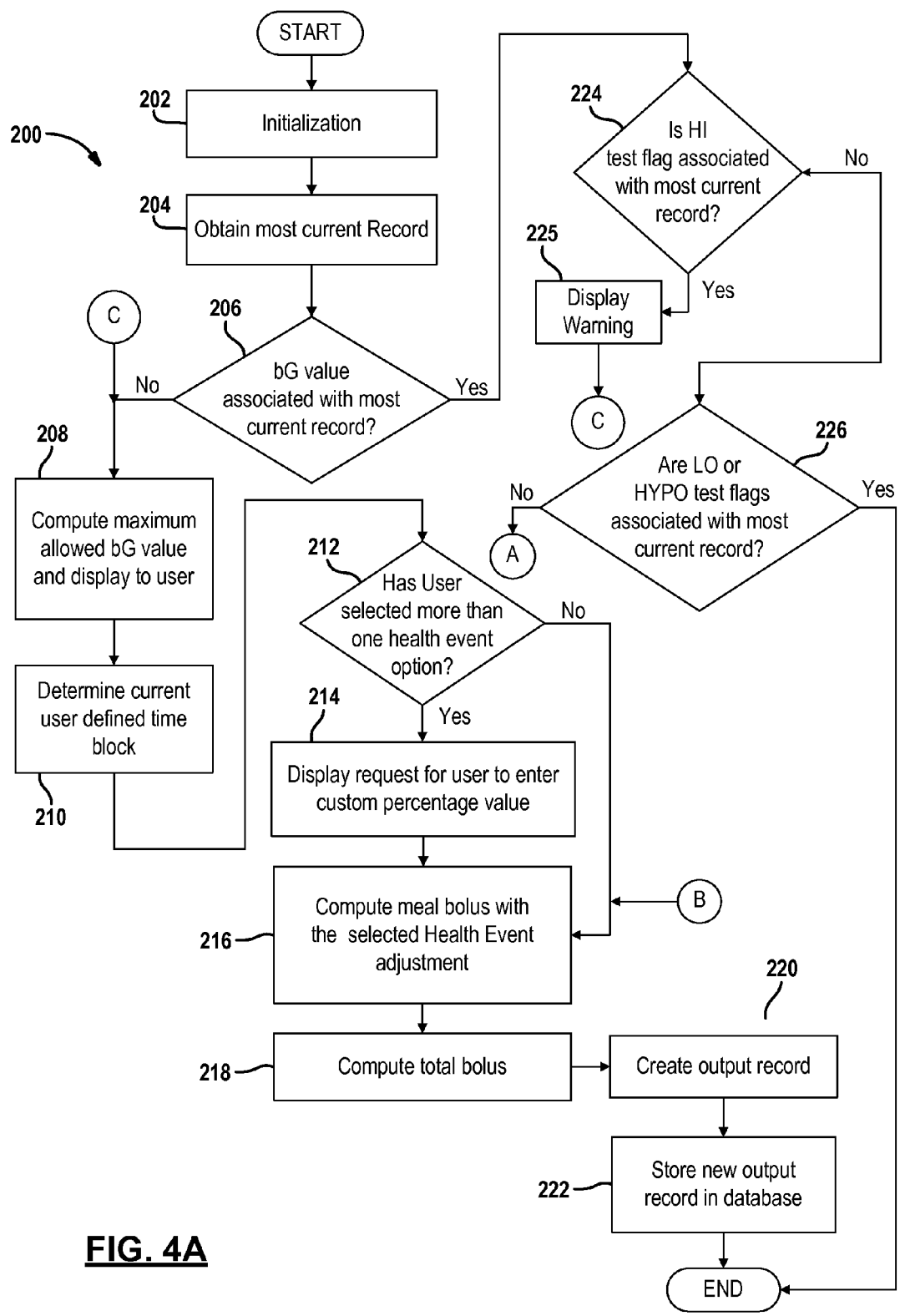
FIGS. 4A and 4B represent an exemplary flowchart illustrating operations that can be performed in computing a total bolus using user defined health adjustment percentages by which the computed meal bolus and computed correction bolus can be modified (by the user) before calculating a recommended total bolus.
Figure 4B:
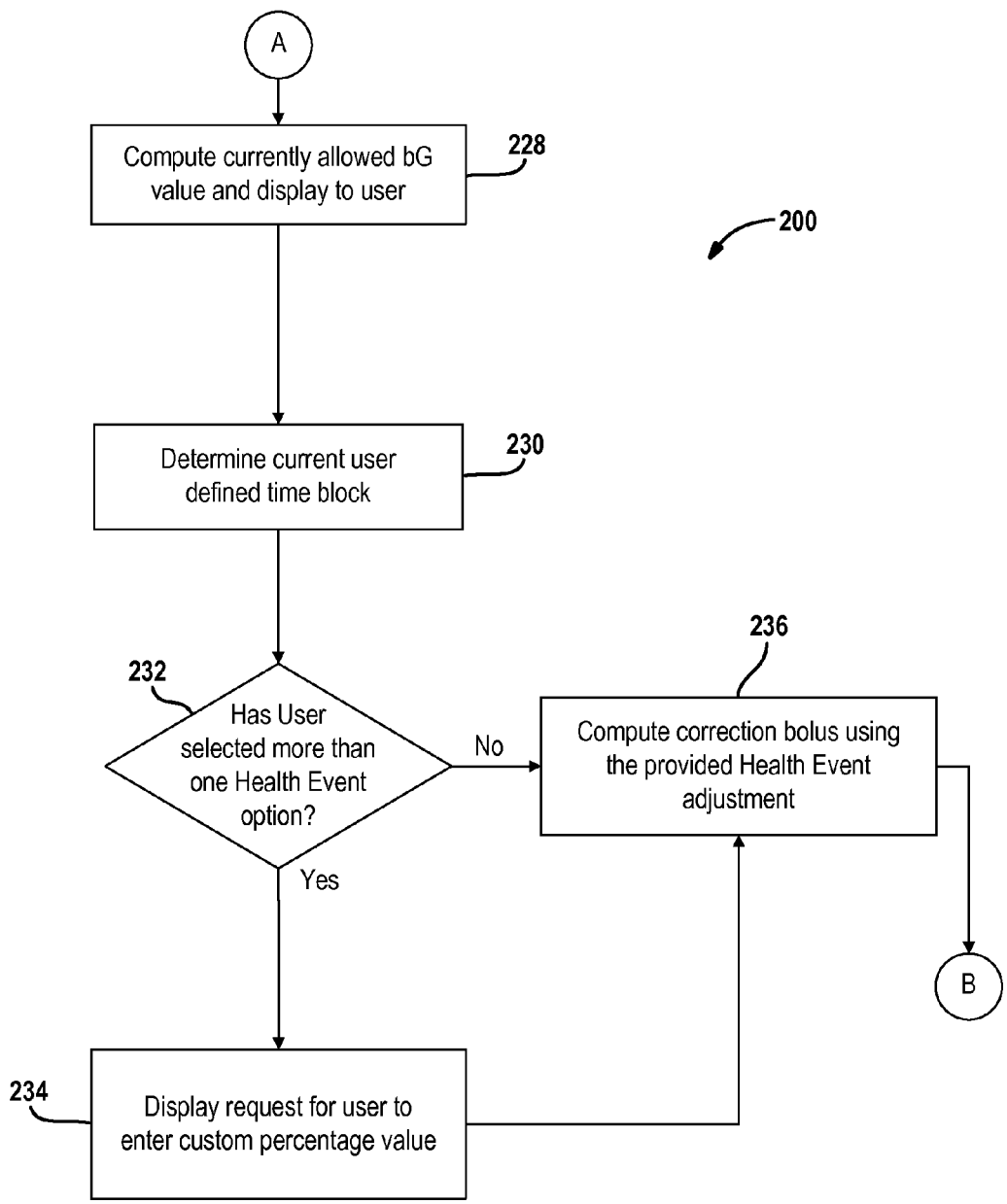

Referring now to FIGS. 4A and 4B, a flowchart 200 is shown of exemplary operations that can be performed by the device 10 in determining a total bolus recommendation for the user that takes into account the configuration programmed into the device 10 by the user. At operation 202 an initialization operation is performed to set the record contents of the processing subsystem 22 to "0". At operation 204 the processing subsystem 22 obtains the most current record stored in the database 26 and checks at operation 206 to determine if it has an associated bG test value. If not, then at operation 208 the maximum allowed bG is computed and displayed to the user. At operation 210 the processing subsystem 22 determines the current time block. At operation 212 the processing subsystem 22 checks to determine if the user has selected more than one health event option and, if the user has selected more than one option, a request is made on the display 16 for the user to enter a custom percentage value, as indicated at operation 214, that will be applied to subsequent meal bolus and correction bolus calculations (because of the formulation this percentage cancels out of the suggested carbohydrate calculation). At operation 216 the processing subsystem 22 will compute the meal bolus and apply the selected health event adjustment defined by the user (if any such adjustment has been selected by the user). At operation 218 the processing subsystem 22 will compute the total bolus. At operation 220 the processing subsystem 22 will update and store the output along with the record in the database 26 at operation 222.

Referring further to FIGS. 4A and 4B, if the check at operation 206 reveals that there is a bG value associated with the most current record, then a check is made at operation 224 to see if the "HI" test flag of the record is set, indicating a bG reading that is above a display limit of the device 10, and which therefore will not be used to calculate a recommended correction bolus. If this check provides a "Yes" answer, then after the display of an appropriate warning at operation 225 for a HI bG reading, operations 208-222 may be performed to obtain only a recommendation for a meal bolus. If the check at operation 224 produces a "No" answer, then a check is made to determine if "LO" or "HYPO" test flags are set for the most current record (Advice Record_IN), as indicated at operation 226. This check indicates either a hypoglycemic condition or a bG reading below the display limit of the device 10. In the event of a "Yes" answer, the routine of flowchart 200 ends (and flowchart 300 shown in FIG. 5 begins for calculating a carbohydrate suggestion). If the check at operation 226 produces a "No" answer, then at operation 228 in FIG. 4B the processing subsystem 22 computes the maximum allowed bG value and displays it to the user on the display 16.

Continuing in FIG. 4B, at operation 230 the processing subsystem 22 determines the current user defined time block. At operation 232 the processing subsystem 22 checks to determine if the user has selected more than one health event option and, if the user has selected more than one option, a request is made on the display 16 for the user to enter a custom percentage value, as indicated at operation 234, that will be applied to the correction bolus calculation at operation 236. At operation 236 the processing subsystem 22 will compute the correction bolus and apply the selected health event adjustment defined by the user (if any such adjustment has been selected by the user). Operations 216-222 from FIG. 4A will then be repeated. If the check at operation 232 produces a "No" answer, the operation 236 will be performed using the user set healthy event adjustment.

Figure 5:
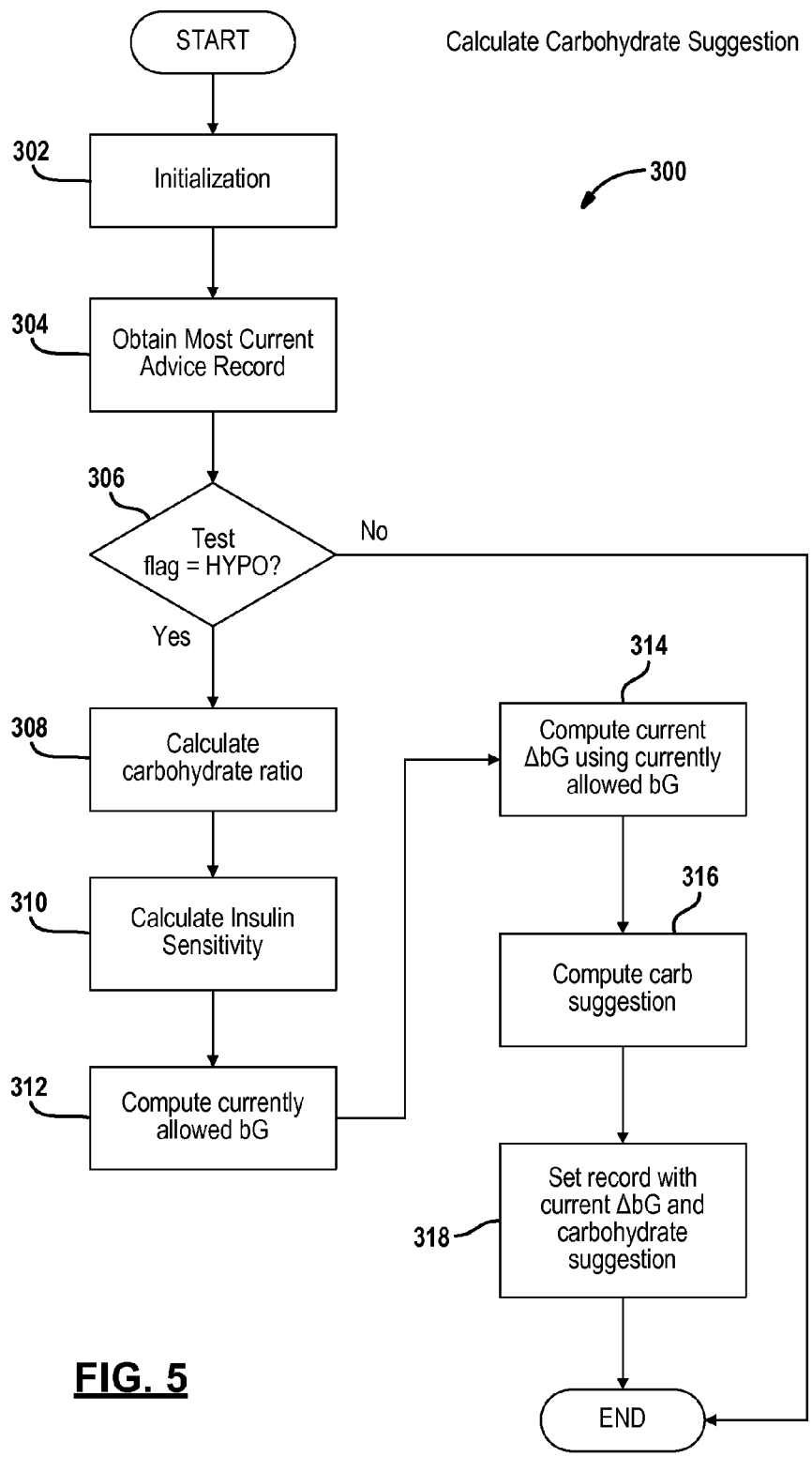
FIG. 5 is an exemplary flowchart illustrating operations that can be performed by the device of FIG. 1 in calculating a carbohydrate suggestion for the user.

Turning to FIG. 5, a flowchart 300 is shown illustrating exemplary operations to show a carbohydrate suggestion can be calculated using the device 10 (this flow occurs based on the "Yes" path at operation 230 in FIG. 4A). At operation 302 an initialization procedure is performed to ensure that any pre-existing data that may be present in the output contents of the processing subsystem 22 is cleared. The most current record is then obtained at operation 304. At operation 306 a check is made to determine if the HYPO test flag of the most current record is set, indicating a hypoglycemic condition for the current bG test value being analyzed. If so, the processing subsystem 22 computes the carbohydrate ("carb") ratio at operation 308 in the traditional manner. At operation 310 the insulin sensitivity is calculated in the traditional manner. At operation 312 the currently allowed bG is computed. At operation 314 the current delta bG is computed by subtracting the currently allowed bG from the most current record bG concentration. This is different from previous bG computation methodologies, which involved subtracting the bG value at the center of the user set bG target range. So in effect, operation 314 allows a previously taken correction bolus, which would operate to lower the user's bG, to be factored into the equation for determining the current delta bG. At operation 316 the current delta bG is converted into a carbohydrate suggestion using the insulin sensitivity and by the carbohydrate ratio factors. At operation 318 the outputs of carbohydrate suggestion and current delta bG are stored.

Figure 6:
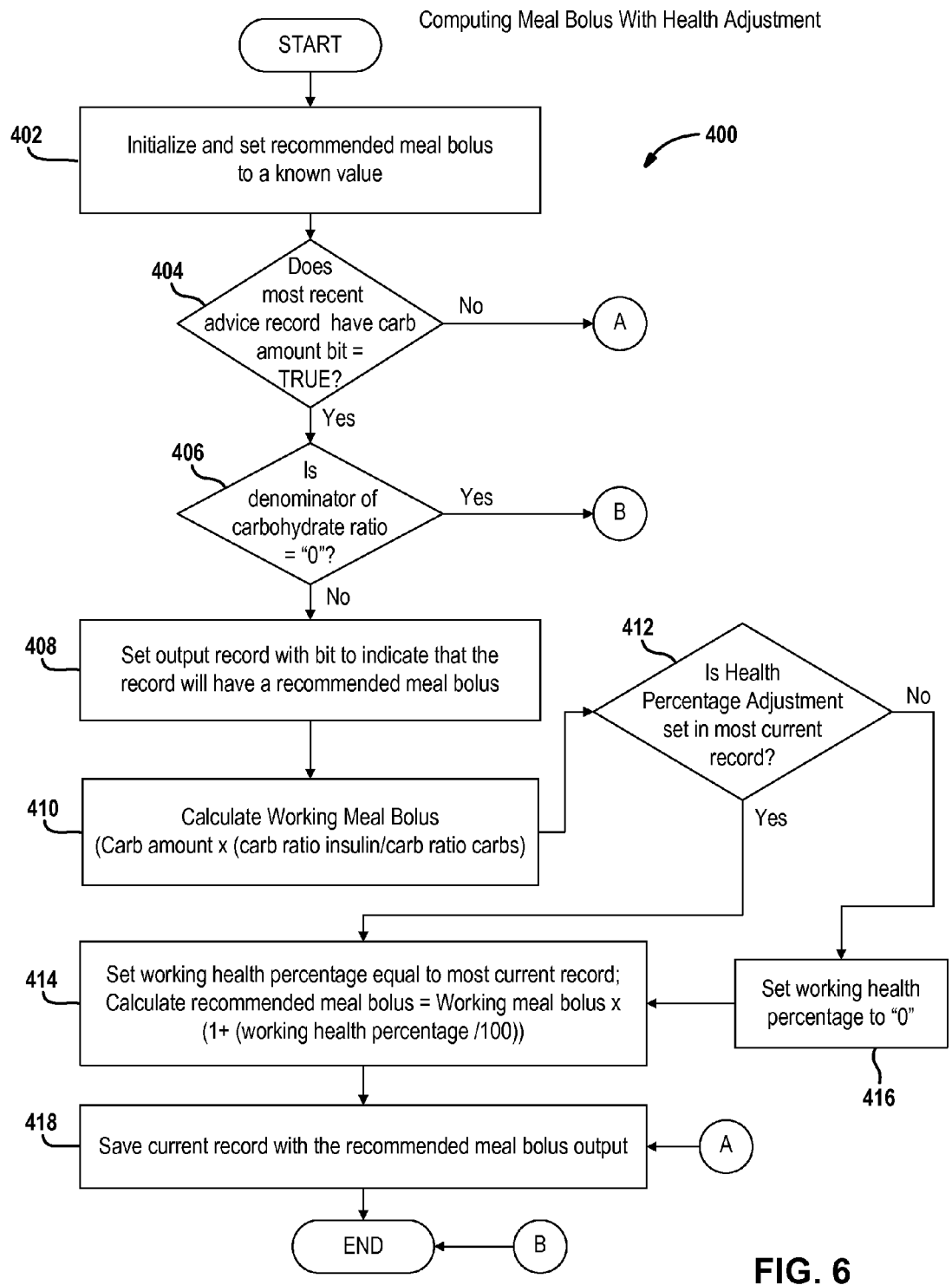
FIG. 6 is a flowchart illustrating exemplary operation performed by the device of FIG. 1 in computing the recommended meal bolus with a user programmed health adjustment applied thereto.

Referring now to FIG. 6, a flowchart 400 is shown illustrating one exemplary manner of computing a meal bolus with a health event adjustment (this flow is called out at operation 220 of FIG. 4B). At operation 402 an initialization is performed to set the recommended meal bolus to a known value. At operation 404 a check is made to determine if the most current record retrieved by the processing subsystem 22 from the database 26 has a carbohydrate amount available for use in the following calculations. If the answer is "Yes", then at operation 406 a check is made to ensure that the denominator of the carbohydrate ratio is not "0". If it is not, then at operation 408 a bit will be set for the output being created by the processing subsystem 22 to indicate a recommended meal bolus is associated with it. At operation 410 the working meal bolus is calculated. At operation 412 a check is made if a health event adjustment percentage is set in the most current record. If so, then at operation 414 a working health percentage is set equal to the health percentage contained in the most current record, and the recommended meal bolus is calculated using this working health percentage. For example, if the user has indicated "−20" in her/his percentage adjustment for the associated health event, then operation 414 uses this information to convert the "−20" to 80%, and the 80% figure is used to modify the working meal bolus to come up with the recommended meal bolus. Thus, in this example, the recommended meal bolus would be reduced by 20%. At operation 418 the recommended meal bolus output just created by the processing subsystem 22 is saved in the log records portion 26a of the database 26.

If the check at operation 412 indicates that no health percentage adjustment is indicated in the most current record, then the working health adjustment percentage is set equal to zero at operation 416 and then operations 414 and 418 are repeated. If in operation 404 it is understood that there is no carbohydrate amount from which a recommended meal bolus can be calculated, the recommended meal bolus of zero is simply saved at operation 418. If the denominator of the carbohydrate ratio of the most current record is found to be "0" at operation 406, then the routine ends with an error condition.

Figure 7:
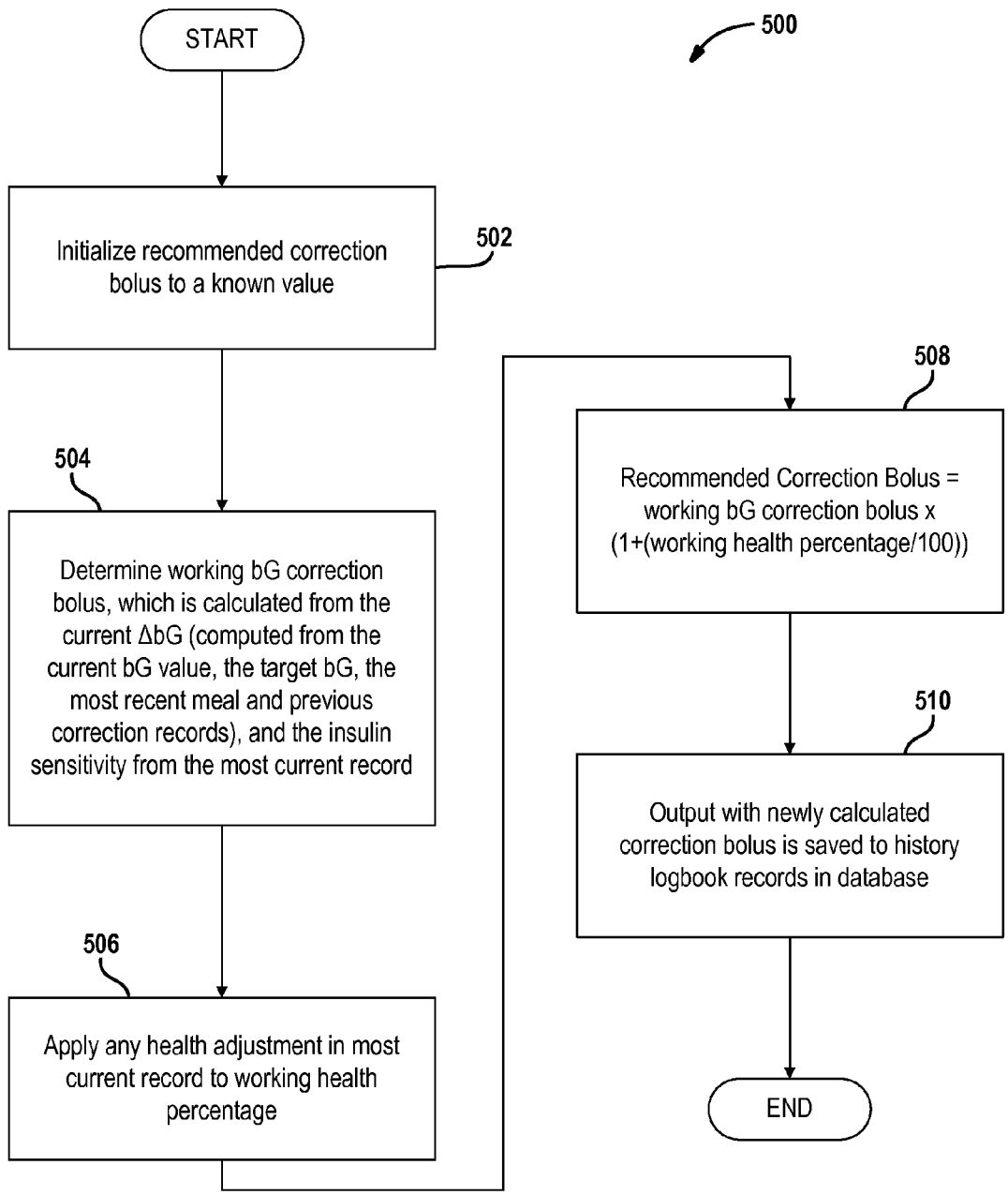
FIG. 7 is a flowchart illustrating exemplary operations that can be performed in computing a recommended correction bolus with a health adjustment percentage set by the user.

Referring to FIG. 7, there is shown an exemplary flowchart 500 setting forth operations that can be performed in computing a correction bolus, taking into account a percentage health adjustment input by the user. It will be appreciated that the operations of flowchart 500 are called by operation 236 in FIG. 4B.

At operation 502 the recommended correction bolus is initialized to a known value. At operation 504 the working bG correction bolus is calculated from the current delta bG (computed from the current bG value, the target bG, the most recent meal and previous correction records), and the insulin sensitivity from the most current record. At operation 506 any health adjustment percentage present in the most current record is applied to the working health percentage. Again, if the user has specified "None" when selecting a health adjustment percentage for the bG test value associated with the most current record, then the working health percentage will not be modified by any percentage value. At operation 508 the recommended correction bolus is obtained by modifying the working bG correction bolus by the health percentage adjustment. Thus, if the user had set the health adjustment percentage for the bG test value associated with the most current record to "−25", then the calculation at operation 508 would multiply the working bG correction bolus by 75%. The output with the newly calculated recommended correction bolus is then saved to the database history logbook records 26a at operation 510.

In calculating the correction delta bG, an advantage of the device 10 is that the working delta bG is allowed to be a negative value. This allows a portion of any correction to be removed from the newly calculated correction delta bG, such as if the user had previously taken some carbohydrates to compensate for a LO or HYPO bG value, to be factored into the newly calculated correction delta bG. Another advantage is that for computing a carbohydrate suggestion for the user, the recommendations can be calculated to the currently allowed bG value rather than to the center of the bG target range.

In one implementation the present disclosure relates to a method for monitoring blood glucose (bG) levels of a diabetic user. The method may be implemented on a non-transitory computer readable medium adapted to run on a processing subsystem, the processing subsystem forming a portion of a handheld diabetes management device for monitoring the bG levels of a diabetic user and determining a correction bolus to be provided to the user. The method may comprise using a memory to store information in a plurality of different time blocks. The information may include: an upper target bG value for each one of the plurality of different time blocks, defined by the user, during a twenty four hour period; a lower target bG value for each one of the plurality of different time blocks during the twenty four hour period; a hypoglycemic warning value, defined by the user, representing a hypoglycemic bG value for the user; a conversion factor for converting from glucose to insulin; a plurality of differing user defined health events that each include a predetermined associated percentage value set by the user by which a correction bolus calculation will each be modified to account for one of an increase or a decrease in insulin associated with each one of the differing health events; and a carbohydrate value input by the user in connection with a meal. The processing subsystem may be used to communicate with the memory and to obtain the information and to calculate therefrom the correction bolus.

The method may further comprise using the predetermined associated percentage values of the user defined health events in calculating a meal bolus, and using a conversion factor for converting the carbohydrate value to a corresponding insulin value.

The method may further comprise enabling the user to define and store in the memory different insulin sensitivity and carbohydrate ratio values for each one of the plurality of time blocks.

The method may further comprise modifying the correction bolus by an insulin sensitivity of the insulin and one of the percentage values associated with one of the health events.

The method may further comprise modifying the calculated meal bolus by a carbohydrate ratio and one of the percentage values associated with one of the health events.

The method may further comprise having the processing subsystem use the information to generate a carbohydrate amount recommendation for the user when the user's bG level is below the hypoglycemic warning value.

The method may further comprise using the processing subsystem to consider an action shape of a previously taken correction bolus, the action shape being defined by a bG lowering potential of the previously taken correction bolus, an offset time of insulin associated with the previously taken correction bolus, and an acting time of the insulin associated with the previously taken correction bolus, and the action shape being considered by the processing subsystem when generating a new bolus recommendation.

The method may further comprise having the action shape considered by the processing subsystem when generating a carbohydrate suggestion.

The method may further comprise using the processing subsystem to consider an action shape of a last previous meal, the action shape being defined by a meal rise glucose amplitude, an offset time of the last previous meal, an acting time of the last previous meal, and the action shape being considered by the processing subsystem when generating a new bolus recommendation.

The method may further comprise using the processing subsystem to receive as inputs from the user, the acting time and the offset time.

The method may further comprise using the processing subsystem to receive as inputs from the user a meal rise glucose amplitude, acting time and offset time.

The method may further comprise the plurality of user defined differing health events including custom user selected and user named health events including at least one of an exercise event, a stress event, an illness event and a periodic physiological cycle event.

The method may further comprise recommending, displaying and allowing the modification of the correction bolus, a meal bolus and a total bolus to the user on a visual display of the device.

In another implementation the present disclosure relates to a method implemented on a non-transitory computer readable medium adapted to run on a processing subsystem, the processing subsystem forming a portion of a handheld diabetes management device for monitoring blood glucose (bG) levels of a diabetic user and determining a total bolus to be provided to the user. The method may comprise using a memory to store: an upper target bG value for each one of a plurality of different time blocks during a twenty four hour period; a lower target bG value for each one of the plurality of different time blocks during the twenty four hour period; a maximum allowed bG value representing a currently corrected for bG value of the user, which is computed from prior bG history records; a plurality of user defined health events including an exercise event, a stress event and an illness event, with each one of the health events including a predetermined associated percentage value selected by the user by which a preliminary bolus calculation will be modified to account for one of an increase or a decrease in insulin associated with the health event; and a carbohydrate value input by the user in connection with a meal. The processing subsystem may be used to communicate with the memory and obtain the upper target bG value, the lower target bG value, the maximum allowed bG value, one of the user defined health events, and the carbohydrate value input by the user; and to calculate therefrom: a meal bolus calculated based on the carbohydrate value input by the user, the meal bolus representing an amount of insulin needed to compensate for the carbohydrate value representing the meal; a correction bolus representing an additional amount of insulin needed beyond the insulin represented by the meal bolus; and a total bolus value obtained by summing the meal bolus and the correction bolus to obtain a summed bolus value. And then, for each of the meal bolus and the correction bolus, the summed bolus value may be modified in accordance with the percentage value of a user selected one of the user defined health events. The correction bolus, the meal bolus, the total bolus value and the maximum allowed bG value may be displayed to the user on a display of the device.

The method may further comprise having the processing subsystem adapted to consider, in determining the maximum allowed bG value and a currently allowed bG value, the following: an offset time, input by the user, for insulin being taken by the user, before generating a new bolus recommendation; and an acting time, input by the user, for insulin being taken by the user, before generating a new bolus recommendation.

The method may further involve having the processing subsystem adapted to use the information to generate a carbohydrate amount recommendation for the user when the user's bG level is below a hypoglycemic warning value for the user.

In still another aspect the present disclosure relates to a customizable, handheld diabetes management device for monitoring blood glucose (bG) levels of a diabetic user and determining a total bolus to be provided to the user. The device may comprise a housing adapted to be held in a hand of the user, and a memory contained in the housing and configured to store information including: an upper target bG value for each one of a plurality of different time blocks defined by the user during a twenty four hour period; a lower target bG value for each one of the plurality of different time blocks during the twenty four hour period; a plurality of differing user defined health events that each include a predetermined associated percentage value set by the user by which a meal bolus calculation and a correction bolus calculation will each be modified to account for one of an increase or a decrease in insulin associated with each one of the differing health events; and a carbohydrate value input by the user in connection with a meal. A processing subsystem contained in the housing is in communication with the memory. The processing subsystem is adapted to obtain the information from the memory and to calculate therefrom the meal bolus, the correction bolus and a recommended total bolus that is a sum of the calculated meal bolus and the calculated correction bolus. A display system contained in the housing may be used for displaying a plurality of fields that the user is able to configure to include the information, and also for displaying the recommended total bolus to the user.

The system may further include the information comprising insulin sensitivity information pertaining to the user, the insulin sensitivity information being input by the user and used by the processing subsystem to modify the calculated correction bolus.

The system may also include the insulin sensitivity information comprising a plurality of differing insulin sensitivities input by the user for different ones of the plurality of different time blocks.

The system may also include the calculated correction bolus being modified by one of the insulin sensitivities and the percentage value associated with one of the user defined health events.

The system may also include the calculated meal bolus being modified by the carbohydrate ratio and the percentage value associated with one of the user defined health events.

The system may also include the processing subsystem further being adapted to use the information to generate a carbohydrate amount recommendation for the user when the user's bG level is below a hypoglycemic warning limit.

The system may also include the processing subsystem being further adapted to consider an acting time, input by the user, for insulin being taken by the user, before generating a new bolus recommendation.

The system may also include the processing subsystem being further adapted to consider an offset time, input by the user, for insulin being taken by the user, before generating a new bolus recommendation.

The system may also include the plurality of user defined differing health events comprising custom user selected and user named health events that include at least one of an exercise event, a stress event, an illness event and a periodic physiological cycle event.

The examples illustrate the various embodiments and are not intended to limit the present disclosure. Therefore, the description and claims should be interpreted liberally with only such limitation as is necessary in view of the pertinent prior art.

One skilled in the art will appreciate that the teachings can be practiced with embodiments other than those disclosed. The disclosed embodiments are presented for purposes of illustration and not limitation, and the invention is only limited by the claims that follow.

What is claimed is:

1. A method implemented on a non-transitory computer readable medium adapted to run on a processing subsystem, the processing subsystem forming a portion of a handheld diabetes management device for monitoring blood glucose (bG) levels of a diabetic user and determining a correction bolus to be provided to the user, the method comprising:
using a memory to store information in a plurality of different time blocks, the information including:
an upper target bG value for each one of the plurality of different time blocks, defined by the user, during a twenty four hour period;
a lower target bG value for each one of the plurality of different time blocks during the twenty four hour period;
a hypoglycemic warning value, defined by the user, representing a hypoglycemic bG value for the user;
a conversion factor for converting from glucose to insulin;
one or more health events which can be associated by the user with a request for an insulin recommendation, where each health event includes a percentage value set by the user; and
a carbohydrate value input by the user in connection with a meal;
receiving, by a processor of the processing subsystem, a request for an insulin recommendation for a patient;
determining, by the processor, how many health events are associated with the request for an insulin recommendation;
prompting, by the processor, the user for an input for the health events associated with the insulin recommendation, where the prompting is in response to a determination that two or more health events are associated with the request for an insulin recommendation;
receiving, by the processor, an input value from the user in response to the prompting, where the input is a numeric value representing a cumulative effect of the health events on the insulin of the patient; and
computing, by the processor, the correction bolus for the patient based on the input value.

2. The method of claim 1, further comprising calculating a meal bolus using a conversion factor for converting the carbohydrate value to a corresponding insulin value.

3. The method of claim 2, further comprising enabling the user to define and store in the memory different insulin sensitivity and carbohydrate ratio values for each one of the plurality of time blocks.

4. The method of claim 3, wherein the correction bolus is modified by an insulin sensitivity of the insulin and one of the percentage values associated with one of the health events.

5. The method of claim 2, wherein the calculated meal bolus is modified by a carbohydrate ratio and one of the percentage values associated with one of the health events.

6. The method of claim 1, further comprising using the processing subsystem to use the information to generate a carbohydrate amount recommendation for the user when the user's bG level is below the hypoglycemic warning value.

7. The method of claim 1, further comprising using the processing subsystem to consider an action shape of a previously taken correction bolus, the action shape being defined by a bG lowering potential of the previously taken correction bolus, an offset time of insulin associated with the previously taken correction bolus, and an acting time of the insulin associated with the previously taken correction bolus, and the action shape being considered by the processing subsystem when generating a new bolus recommendation.

8. The method of claim 7, wherein the action shape is considered by the processing subsystem when generating a carbohydrate suggestion.

9. The method of claim 1, further comprising using the processing subsystem to consider an action shape of a last previous meal, the action shape being defined by a meal rise glucose amplitude, an offset time of the last previous meal, an acting time of the last previous meal, and the action shape being considered by the processing subsystem when generating a new bolus recommendation.

10. The method of claim 7, further comprising using the processing subsystem to receive as inputs from the user, the acting time and the offset time.

11. The method of claim 9, further comprising using the processing subsystem to receive as inputs from the user a meal rise glucose amplitude, acting time and offset time.

12. The method of claim 1, wherein the plurality of user defined differing health events comprise custom user selected and user named health events including at least one of an exercise event, a stress event, an illness event and a periodic physiological cycle event.

13. The method of claim 1, further comprising recommending, displaying and allowing the modification of the correction bolus, a meal bolus and a total bolus to the user on a visual display of the device.

14. A method implemented on a non-transitory computer readable medium adapted to run on a processing subsystem, the processing subsystem forming a portion of a handheld diabetes management device for monitoring blood glucose (bG) levels of a diabetic user and determining a total bolus to be provided to the user, the method comprising:

using a memory to store:
- an upper target bG value for each one of a plurality of different time blocks during a twenty four hour period;
- a lower target bG value for each one of the plurality of different time blocks during the twenty four hour period;
- a maximum allowed bG value representing a currently corrected for bG value of the user, which is computed from prior bG history records;
- one or more health events which can be associated by the user with a request for an insulin recommendation, where health events include an exercise event, a stress event and an illness event and each health event includes a percentage value set by the user;
- a carbohydrate value input by the user in connection with a meal;

receiving, by a processor of the processing subsystem, a request for an insulin recommendation for a patient;

determining, by the processor, how many health events are associated with the request for an insulin recommendation;

prompting, by the processor, the user for an input for the health events associated with the insulin recommendation, where the prompting is in response to a determination that two or more health events are associated with the request for an insulin recommendation;

receiving, by the processor, an input value from the user in response to the prompting, where the input is a numeric value representing a cumulative effect of the health events on the insulin of the patient;

calculating, by the processor, a meal bolus based on the carbohydrate value input by the user, the meal bolus representing an amount of insulin needed to compensate for the carbohydrate value representing the meal;

calculating, by the processor, a correction bolus representing an additional amount of insulin needed beyond the insulin represented by the meal bolus;

summing the meal bolus and the correction bolus to obtain a summed total bolus value; and displaying the correction bolus, the meal bolus, the total bolus value and the maximum allowed bG value to the user on a display of the device.

15. The method of claim 14, wherein the processing subsystem further is adapted to consider, in determining the maximum allowed bG value and a currently allowed bG value, the following:
- an offset time, input by the user, for insulin being taken by the user, before generating a new bolus recommendation; and
- an acting time, input by the user, for insulin being taken by the user, before generating a new bolus recommendation.

16. The method of claim 14, wherein the processing subsystem further is adapted to use the information to generate a carbohydrate amount recommendation for the user when the user's bG level is below a hypoglycemic warning value for the user.

17. A customizable, handheld diabetes management device for monitoring blood glucose (bG) levels of a diabetic user and determining a total bolus to be provided to the user, the device comprising:

a housing adapted to be held in a hand of the user;

a memory contained in the housing and configured to store information including:
- an upper target bG value for each one of a plurality of different time blocks defined by the user during a twenty four hour period;
- a lower target bG value for each one of the plurality of different time blocks during the twenty four hour period;
- one or more health events which can be associated by the user with a request for an insulin recommendation, where health events include an exercise event, a stress event and an illness event and each health event includes a percentage value set by the user; and
- a carbohydrate value input by the user in connection with a meal;

a processing subsystem contained in the housing and being in communication with the memory, the processing subsystem configured to receive a request for an insulin recommendation for a patient, determine how many health events are associated with the request for an insulin recommendation and prompt the user for an input for the health events associated with the insulin recommendation, where the prompting is in response to a determination that two or more health events are associated with the request for an insulin recommendation;

the processing subsystem further configured to receive an input value from the user in response to the prompting, where the input is a numeric value representing a cumulative effect of the health events on the insulin of the patient and calculate a meal bolus, a correction bolus and a recommended total bolus that is a sum of the meal bolus and the correction bolus; and a display system contained in the housing for displaying a plurality of fields that the user is able to configure to include the information, and for displaying the recommended total bolus to the user.

18. The system of claim 17, wherein the information further comprises insulin sensitivity information pertaining to the user, the insulin sensitivity information being input by the user and used by the processing subsystem to modify the calculated correction bolus.

19. The system of claim 18, wherein the insulin sensitivity information comprises a plurality of differing insulin sensitivities input by the user for different ones of the plurality of different time blocks.

20. The system of claim 19, wherein the calculated correction bolus is modified by one of the insulin sensitivities and the percentage value associated with one of the user defined health events.

21. The system of claim 19, wherein the calculated meal bolus is modified by the carbohydrate ratio and the percentage value associated with one of the user defined health events.

22. The system of claim 17, wherein the processing subsystem further is adapted to use the information to generate a carbohydrate amount recommendation for the user when the user's bG level is below a hypoglycemic warning limit.

23. The system of claim 17, wherein the processing subsystem further is adapted to consider an acting time, input by the user, for insulin being taken by the user, before generating a new bolus recommendation.

24. The system of claim 23, wherein the processing subsystem further is adapted to consider an offset time, input by the user, for insulin being taken by the user, before generating a new bolus recommendation.

25. The system of claim 17, wherein the plurality of user defined differing health events comprise custom user selected and user named health events that include at least one of an exercise event, a stress event, an illness event and a periodic physiological cycle event.

* * * * *